United States Patent
Andersson et al.

(10) Patent No.: US 7,925,374 B2
(45) Date of Patent: Apr. 12, 2011

(54) SYSTEM AND ARRANGEMENT FOR PRODUCING A DENTAL REPLACEMENT COMPONENT, AND SUCH A COMPONENT

(75) Inventors: Matts Andersson, Lerum (SE); Per-Olof Karlsson, Alingsas (SE); Urban Nilsson, Holta (SE)

(73) Assignee: Nobel Biocare Services AG (CH)

( * ) Notice: Subject to any disclaimer, the term of this patent is extended or adjusted under 35 U.S.C. 154(b) by 0 days.

(21) Appl. No.: 10/579,260

(22) PCT Filed: Nov. 4, 2004

(86) PCT No.: PCT/SE2004/001597
§ 371 (c)(1),
(2), (4) Date: Mar. 12, 2007

(87) PCT Pub. No.: WO2005/046502
PCT Pub. Date: May 26, 2005

(65) Prior Publication Data
US 2007/0281284 A1    Dec. 6, 2007

(30) Foreign Application Priority Data

Nov. 12, 2003 (SE) .................................. 0302971

(51) Int. Cl.
*G06F 19/00* (2006.01)
*A61C 13/20* (2006.01)
*A61C 13/08* (2006.01)
*A61C 5/10* (2006.01)
*B28B 7/10* (2006.01)

(52) U.S. Cl. ............. 700/206; 700/98; 700/119; 264/17; 264/19; 264/334; 433/223

(58) Field of Classification Search ............... 433/223, 433/218, 18, 172, 202.1, 213; 264/17–20; 700/98, 119, 206
See application file for complete search history.

(56) References Cited

U.S. PATENT DOCUMENTS
3,861,044 A * 1/1975 Swinson, Jr. ............... 433/218
(Continued)

FOREIGN PATENT DOCUMENTS
WO    WO 9404089 A1    3/1994
(Continued)

OTHER PUBLICATIONS
International Search Report for Application No. PCT/SE2004/001597 (the PCT Counterpart of the parent application) mailed Feb. 17, 2005.

*Primary Examiner* — Cris L Rodriguez
*Assistant Examiner* — Michael R Ballinger
(74) *Attorney, Agent, or Firm* — Knobbe, Martens, Olson & Bear, LLP (57) ABSTRACT

A system for production of a dental crown (23, 24) includes identification equipment (2), modeling equipment (9), ordering equipment (6), and an automated production arrangement (16). The latter, as a function of one or more first information items, is arranged to effect production, by means of pressing or pressure-casting, of an integrated dental crown which is made up of two layers. The first layer comprises or consists of porcelain material, and the second layer consists of aluminum oxide, zirconium oxide, etc. The second layer forms a cap, via which the dental crown can be applied to a tooth stump (28) of a patient (1). The invention also relates to a dental replacement component consisting of the dental crown. It relates also to an arrangement used for a preliminary stage in production of a dental crown, which arrangement is characterized by a cylinder-shaped unit (puck) which is made of porcelain material and can be pressed against the cap under vacuum and at high pressure in order to form the first layer. The invention permits accelerated and efficient production of individual dental crowns.

16 Claims, 5 Drawing Sheets

U.S. PATENT DOCUMENTS

| | | | |
|---|---|---|---|
| 3,866,321 A * | 2/1975 | Valen | 433/176 |
| 4,155,964 A * | 5/1979 | Aronow | 264/13 |
| 4,411,626 A * | 10/1983 | Becker et al. | 433/223 |
| 5,092,022 A * | 3/1992 | Duret | 29/896.1 |
| 5,224,049 A * | 6/1993 | Mushabac | 700/163 |
| 5,342,201 A * | 8/1994 | Oden | 433/223 |
| 5,851,115 A | 12/1998 | Carlsson et al. | |
| 6,106,747 A * | 8/2000 | Wohlwend | 264/16 |
| 6,322,728 B1 * | 11/2001 | Brodkin et al. | 264/19 |
| 6,354,836 B1 * | 3/2002 | Panzera et al. | 433/215 |
| 6,495,072 B1 * | 12/2002 | Van der Zel | 264/16 |
| 6,575,751 B1 | 6/2003 | Lehmann et al. | |
| 6,869,552 B2 * | 3/2005 | Glidewell | 264/16 |
| 2002/0064745 A1 * | 5/2002 | Schulman et al. | 433/2 |
| 2003/0096214 A1 * | 5/2003 | Luthardt et al. | 433/171 |

FOREIGN PATENT DOCUMENTS

| | | | |
|---|---|---|---|
| WO | WO 0110332 A1 | 2/2001 | |

* cited by examiner

SYSTEM AND ARRANGEMENT FOR PRODUCING A DENTAL REPLACEMENT COMPONENT, AND SUCH A COMPONENT

PRIORITY INFORMATION

This application is a U.S. National Phase of International Application No. PCT/SE2004/001597, filed Nov. 4, 2004, which claims the benefit of Swedish Application No. SE 0302971-7, filed Nov. 12, 2003.

BACKGROUND OF THE INVENTION

1. Field of the Invention

The present invention relates to a system for producing an individually configured dental replacement component. The system can comprise identification equipment for identifying the treatment situation, modeling equipment and ordering equipment, by means of which one or more first information items can be generated as a function of one or more second information items obtained from or with the aid of the identification equipment and/or the modeling equipment. In addition, the system includes an at least substantially fully automated production arrangement which can be of the PROCERA® type and is designed to receive the first information item and, as a function of the latter, realize at least most of the dental replacement component.

2. Description of the Related Art

The invention also relates to a dental replacement component in the form of a dental crown and an arrangement for a preliminary stage of construction of the dental replacement component.

Substantially fully automated arrangements/systems for production of dental products are already known, and reference may in this connection be made in particular to the PROCERA® system. Reference may also be made to the patents obtained by the Applicant of the present patent application and to the submitted patent applications, see inter alia EP 490848 and EP 634150.

It is also already known to produce dental crowns from cast gold, porcelain, titanium, with the aid of the substantially fully automated system, see SE 0203496-5.

SUMMARY OF THE INVENTION

It is also already known per se to form caps of densely sintered aluminum oxide or zirconium oxide and to form cast dental crowns from porcelain.

There is a considerable need to be able to produce dental crowns that only need minimal finishing by dental technicians (dental laboratory) and/or a dentist/dental surgeon. In this connection, it is important that well established materials and known and well established techniques and production equipment can be used without having to make any considerable changes to customary routines, practices, know-how, etc. The dental crown produced must be able to be chosen with the desired color. The present invention aims to solve these problems, among others.

In connection with the production of dental crowns, there is also a considerable need to maintain a high quality of the finished dental crowns. The invention solves this problem as well by proposing that a single supplier of the dental crowns and of their parts will be responsible for the dental crowns in their entirety. Small variations, for example with regard to finish, precision, design, etc., will be able to be achieved, and the dental crowns produced will be able to be subjected to uniform control, which in this way will be easier to perform compared with the case where several parties are involved and responsible for their respective inputs in the dental crown production chain. The invention also solves these problems.

The features which can be regarded as principally characterizing a system according to the invention are that, as a function of the first information item or items mentioned in the introduction, the production arrangement is designed to effect production, by pressing or pressure-casting, of an integrated dental replacement component in the form of one or more dental crowns, each dental crown being made up of two layers, and the first layer, which in turn can be made up of several partial layers, comprises or consists of porcelain material, forming the outer shape or most of the outer shape of the dental crown, and the second layer consists of or comprises a material different than the porcelain material, e.g. aluminum oxide, zirconium oxide, etc., which is inlaid in the porcelain material and forms a cap with an inner shape which with great accuracy, e.g. an accuracy of 0.02-0.1 mm, matches an outer shape (e.g. of a tooth stump) in the treatment situation. In addition, the system is characterized in that the dental crown thus produced in the production arrangement is intended to be transferred for final testing and application at the establishment performing and/or participating in the treatment situation and which possesses or has access to equipment for possible finishing and for fitting the dental crown.

In further developments of the inventive concept it is proposed, inter alia, that the first information item or items mentioned above concerning the dental crown, for example its outer and inner shapes, color, etc., will be present in electronic form and that the electronic information thus obtained will be able to be transmitted via data communication and/or telecommunication links, for example public networks. In one embodiment, identification equipment can record the actual dental situation. A dental crown structure designed for the situation can then be generated by means of computer equipment which is intended to visually present the dental crown structure in interaction with a user of the computer equipment. Alternatively, or in combination with the computer equipment, the dental crown construction can be initiated by means of a conventional waxing-up technique. Further embodiments of the system according to the invention are set out in the attached dependent claims concerning the system.

The features which can principally be regarded as characterizing a dental replacement component in the form of a dental crown are that the dental crown is an integrated unit in two layers, where the first layer comprises or consists of porcelain material which forms or is included in the outer shape or most of the outer shape of the dental crown, and the second layer consists of or comprises a material different than the porcelain material, for example densely sintered aluminum oxide, zirconium oxide, etc., which is placed in the porcelain material and forms a cap with an inner shape which with very great accuracy, e.g. 0.02-0.1 mm, matches an outer shape (e.g. of a tooth stump) in the treatment situation or the patient's mouth.

The features which can principally be regarded as characterizing an arrangement for the preliminary stage of the production of a dental replacement component are that the replacement component consists of a dental crown with integrated outer and inner layers, where the outer layer is intended to form the outer shape of the dental crown and consists of or comprises porcelain material, and the inner layer is intended to form an inner cap in the dental crown/porcelain material. The porcelain material is integrated with the material of the cap by means of a casting procedure with application, in a casting tool, of a cylinder-shaped unit (puck)

made of porcelain material which can be pressed against the cap under vacuum and at high temperature.

By means of what has been proposed above, parties hitherto involved in procedures for production of dental crowns are able to cooperate on the market, but with reduced distribution of the various measures conducted between the parties. The substantially fully automated production arrangement can operate with in principle the same routines for ordering and internal distribution. The two layers on the dental crown concerned can be based on conventional cap production and conventional scanning and casting techniques known per se. In the final result, the dental crown produced can be provided with casting channels which are removed by the dental technician, who can also, if appropriate, provide a finish. Final smoothing in the applied state in the patient's mouth is the work of the dentist/dental surgeon.

BRIEF DESCRIPTION OF THE DRAWINGS

Presently proposed embodiments of a system, a dental replacement component and an arrangement according to the invention will be described below with reference to the attached drawings, in which.

DETAILED DESCRIPTION OF THE PREFERRED EMBODIMENTS

Figures 1, 2:
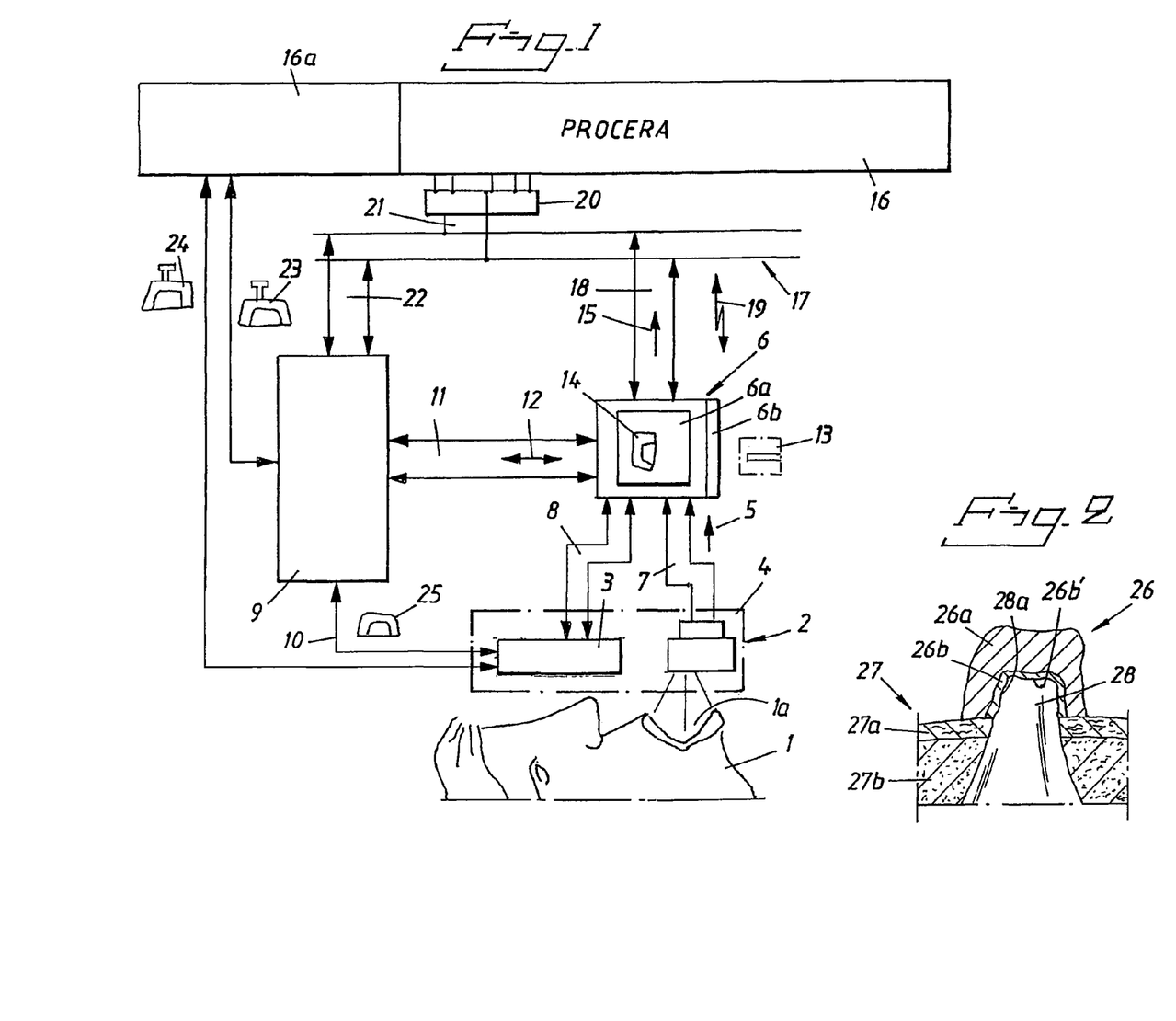
FIG. 1 is a diagrammatic representation showing the system for reading, visual presentation of a dental crown, a dental laboratory, and a fully automated production arrangement for dental crowns.
FIG. 2 is a vertical section showing a dental crown produced by the system according to FIG. 1 and applied in its position on a tooth stump in a patient's jaw bone.

In FIG. 1, a patient is indicated by 1. An individually configured dental crown is to be produced and fitted in the patient's mouth 1a. The system includes identification equipment 2 designed to identify the treatment situation in the patient's mouth 1a. The identification equipment can be of a type known per se and can operate with a camera function, a recording function inside the patient's mouth, in the form of impression-taking, etc. Alternatively, recording can be done in a known manner with the aid of wax casting by the establishment or personnel providing the treatment and symbolized by 3. The treatment can be conducted using equipment known per se and by personnel known per se, such as a dentist/dental surgeon. The equipment 2, 3 can in principle be regarded as belonging to a common installation or establishment 4. With the aid of one or more first information items 5 which are initiated with the aid of the equipment 2 or 3 or the installation as a whole, a computer device symbolized by 6 is supplied. The transmission links are indicated by 7 and 8 and can be configured in one direction or in two directions. FIG. 1 also shows that the equipment or establishment 3 can communicate with an individual in the form of a dental technician (dental technician laboratory) 9. The connection 10 between the units 3 and 9 can be in one direction or in two directions. In one embodiment, the equipment or establishment 9 can be connected to the computer equipment 6 or can possess the computer equipment. This is symbolized by the connection 11, which can once again be in one direction or two directions, see arrow 12. In one embodiment, the computer equipment can be included in or belong to the equipment 4. The computer equipment is provided with a screen 6a and actuating members, for example in the form of a keyboard 6b. By interaction with a user 13, the computer equipment can, as a function of the received information 5, permit visual presentation, on the screen 6a, of a dental crown 14 which is expedient or has been produced for the treatment situation on the patient 1. The identification equipment 2 and the computer equipment 6 can be of types known per se, and the computer equipment can operate with conventional programs and file management, for example known CAD files. The computer equipment is arranged to send an information item or information items 15 to a substantially fully automated production arrangement 16 for dental products. As an example of such an arrangement, mention may be made of PROCERA®. The information item or items 15, here called the first information item or items, can be transmitted via data communication and/or telecommunication links which are indicated symbolically by 17. The connection between the computer equipment 6 and the system 16 can alternatively be completely or partially wireless. A wired connection is indicated by 18, and the wireless connection is indicated by 19. The information item or items 5 are referred to as the second information item or items.

Thus, with the aid of the computer equipment 6, an order can be sent off and registered in the arrangement 16. The arrangement is designed with connection members 20 to said connection system 17. This connection 21 can also be wired and/or wireless. Upon receipt of the first information item or items 15, the order can be registered, after which the arrangement prepares data and sends this to its internal production system, in this case to the unit in the arrangement which is used for production of dental crowns. The order can include the configuration of inner and outer surfaces, color, choice of material, desired delivery time, etc. If so desired, the dental crown can be produced in cooperation with the dental laboratory 9 connected to the arrangement 16 via a connection 22 which can be of the two-way type. The individually configured dental crown produced can be transferred to the establishment 9, and such a dental crown has been indicated by 23. Alternatively, a finished individually configured dental crown can be delivered directly to the establishment 3 intended to fit the dental crown and give it its final shape in the mouth of the patient 1. Such a dental crown is indicated by 24. If the arrangement 16 transfers the crown 23 to the establishment 9, which can then give a final finish to the dental crown, for example, said dental crown is later sent to the establishment 3. Such a transferred and finished crown is indicated by 25. The final shaping and smoothing of the crown 25 is carried out by the establishment 3.

FIG. 2 shows a dental crown 26 which has been produced in the arrangement 16 and has been fitted. It can be fitted on a jaw bone 27 of the patient 1. In FIG. 2, the gum is indicated by 27a and dentine by 27b. The dental crown is fitted on a tooth stump or ground-down tooth 28. The dental crown 26 comprises an outer layer 26a of porcelain and a cap-shaped part 26b arranged in the porcelain material. During production in the arrangement 16, the cap 26b has been configured with an inner surface 26b' corresponding to the outer surface 28a of the tooth.

Figure 3:
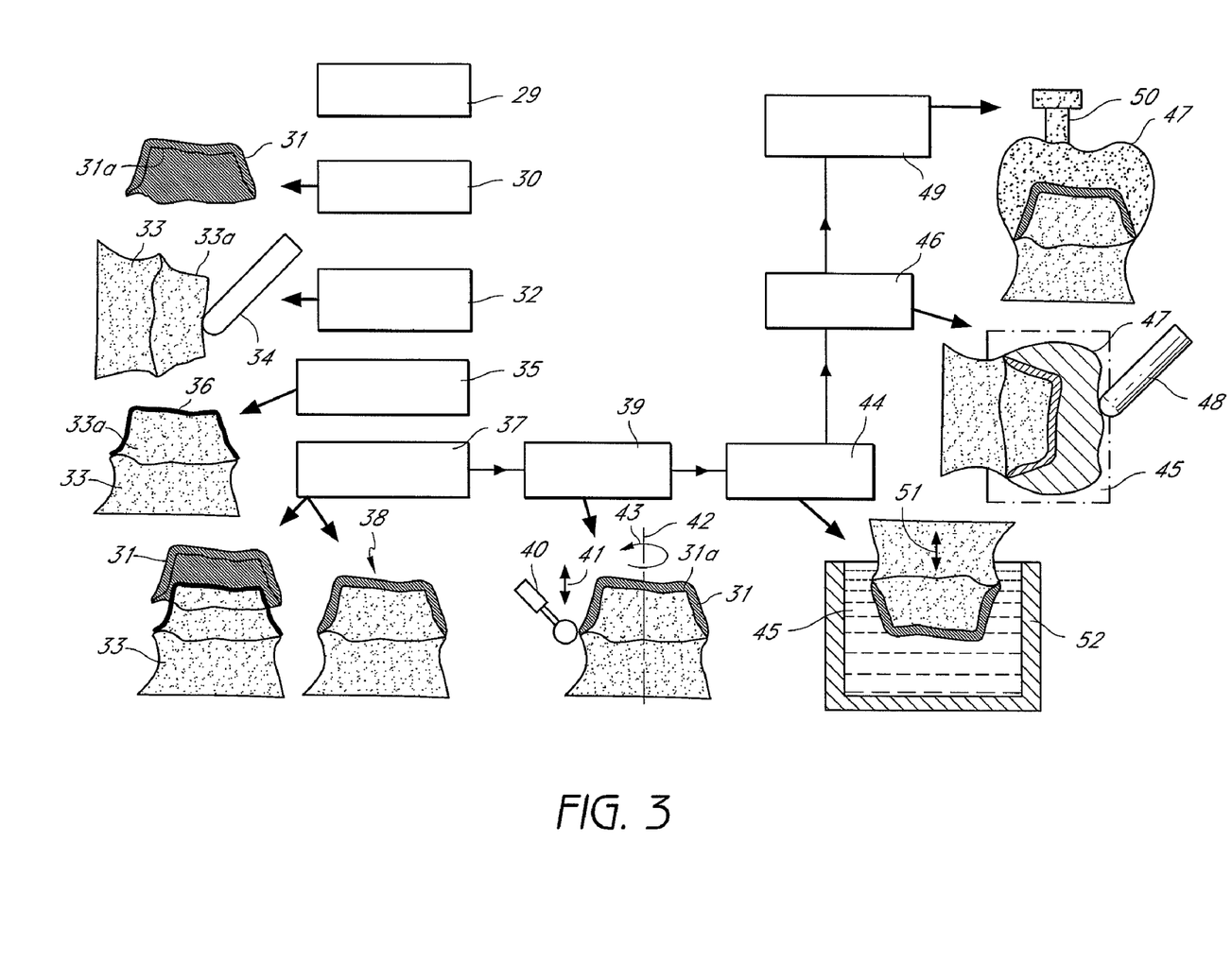
FIG. 3 is a diagrammatic representation showing the production, in successive steps of the production of a mold for a dental crown according to a first illustrative embodiment.

FIG. 3 shows mold production according to a first alternative. In principle, the mold in question can be produced in nine different steps. In a first step 29, the order is placed in accordance with the above at the production unit 16. Data is prepared and sent onward to the internal production system in the unit/equipment 16. In a second step 30, a cap 31 is produced. This production can be effected in a manner known per se, and the cap is made, for example, of aluminum oxide or zirconium oxide. In a subsequent step 32, an embedding compound is shaped so that it is given an outer shape 33a corresponding to the inner shape 31a of the cap 31. The embedding compound is shaped with the aid of a milling tool symbolized by 34. In a step 35, the cap is anchored, for example by applying adhesive 36 to the shaped outer surface 33a of the die 33. In a step 37, the cap 31 is mounted on the die 33 to give a situation indicated by 38. In a subsequent step 39, the outer surface 31a of the die which has been provided with said cap 31 can be scanned. The scanning can be done with a needle or recording member 40 in a manner known per se by vertical displacements of the scanning needle at the same time as the die is rotated about its longitudinal axis 42 in the direction of the arrow 43 (counterclockwise). In a subsequent step 44, the cap and the die are immersed in molten wax or equivalent 45 located in a bath 46. The directions of immersion are indicated by 47. In a step 46, the desired outer shape 47 is milled in the hardened molten wax 45. The milling tool has been symbolized by 48. In the final step 49, a casting channel 50 is applied to the milled mold 47-Alternatively, the casting channels can also be milled from the hardened material.

Figure 4:
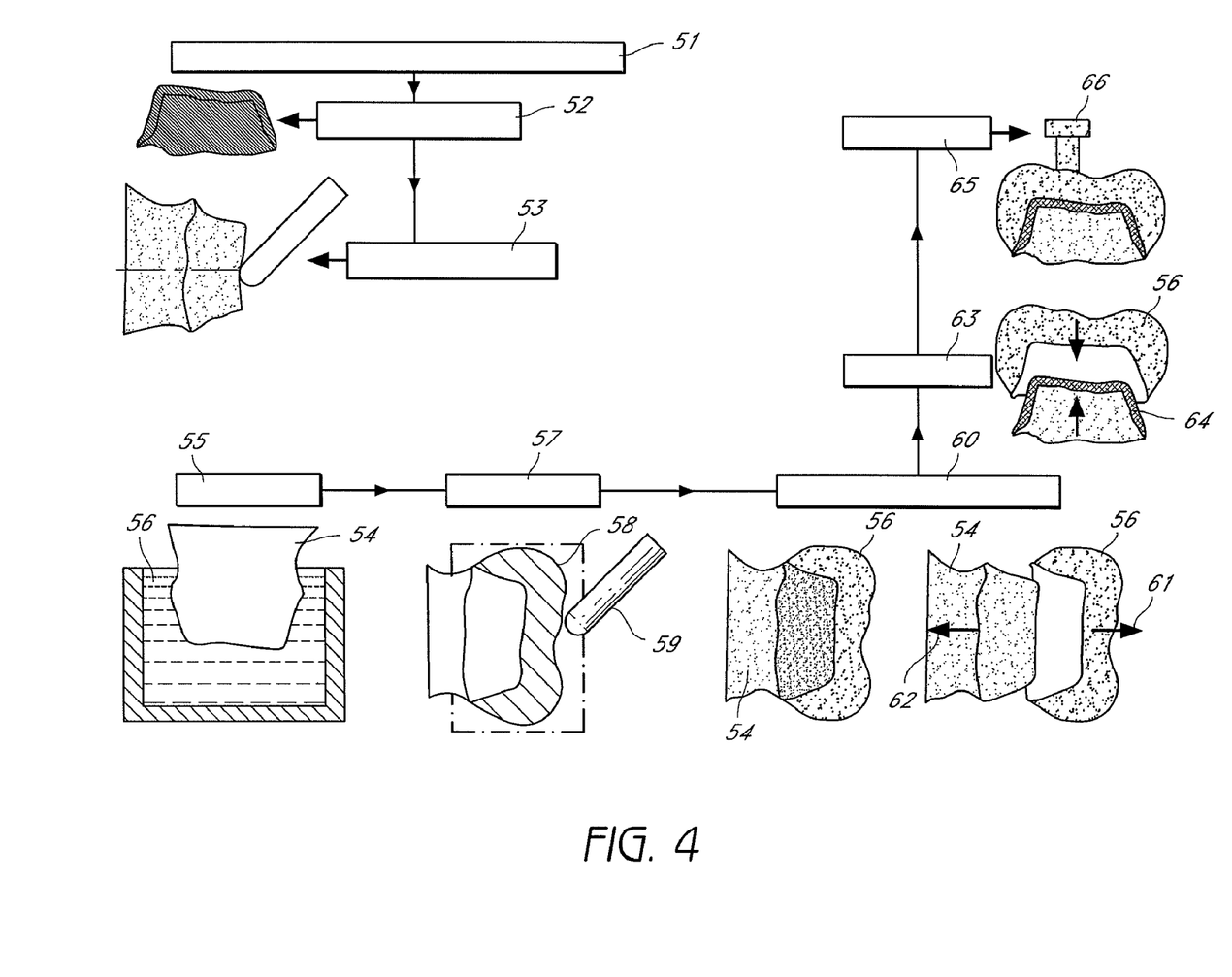
FIG. 4 is a diagrammatic representation showing production of a mold in steps according to a second illustrative embodiment which differs from the illustrative embodiment according to FIG. 3.

In the alternative embodiment for mold production according to FIG. 4, two steps 51 and 52 are used which correspond to steps 29 and 30 in the embodiment according to FIG. 3. A third step 53 involves milling of a die 54 which corresponds to the outer shape of the cap. The material of the die can be graphite, plaster, Teflon, aluminum, etc. In a subsequent step 55, the die 54 is immersed in molten wax 56, and in a subsequent step 57, when the wax has hardened, it is milled so that the outer shape 58 of the crown is obtained. The milling tool is indicated by 59. In a subsequent step 60, the wax mold 56 is separated from the die 54 in the directions of arrows 61 and 62. In a step 63, the cap 64 (see step 52) is joined together with the wax mold 56 to give an assembled configuration as shown by step 65, in which a casting channel is applied or milled.

Figure 5:
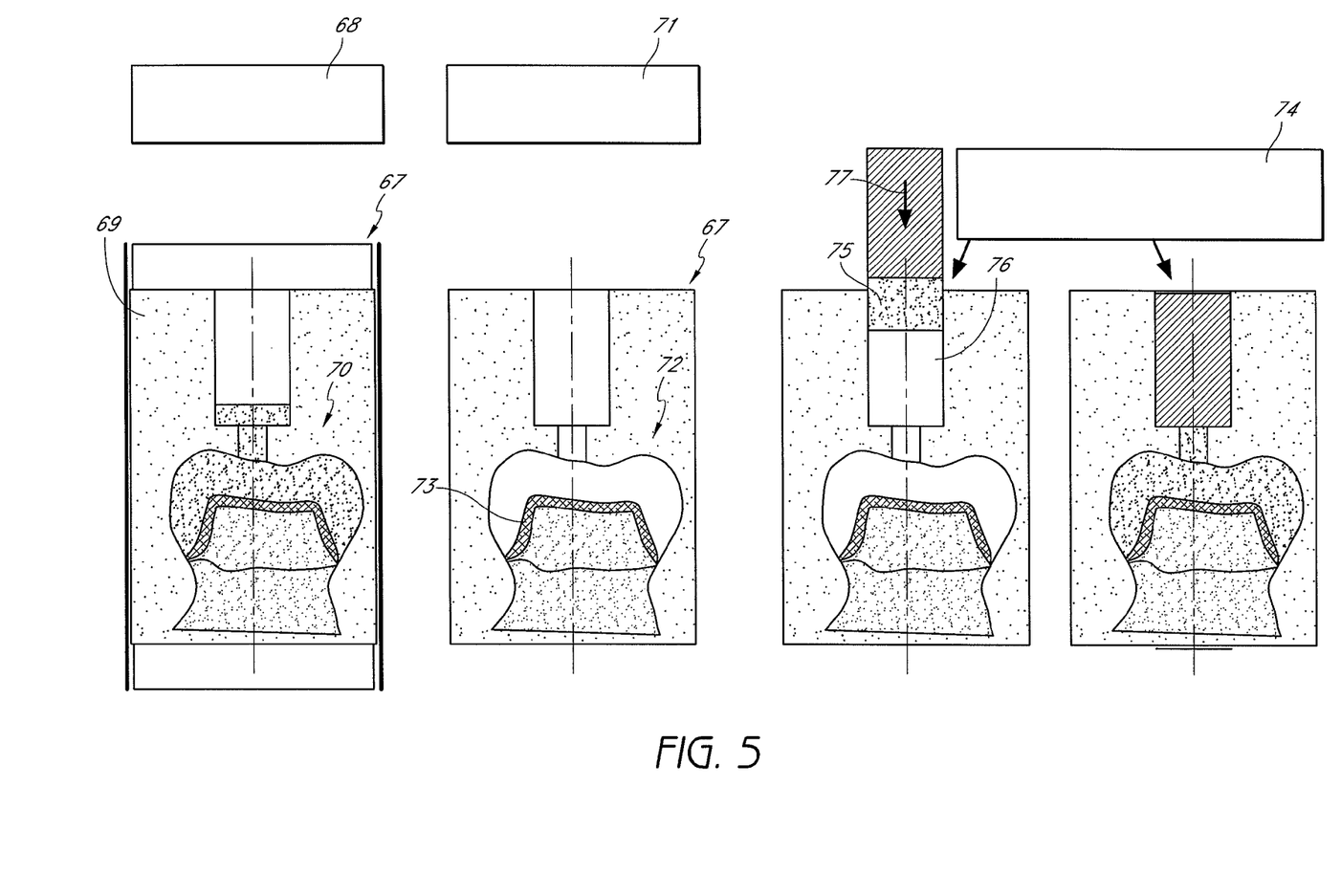
FIG. 5 is a diagrammatic representation showing three different steps in the casting of an outer layer to make a cap for formation of a dental crown.

The mold thus formed in FIGS. 3 and 4 can be used in a cuvette 67 in accordance with FIG. 5. In a step 68, an embedding compound 69 is placed in the cuvette. The mold is indicated by 70 in said embedding compound. In a subsequent step 71, the wax is burned out from the cuvette so that the mold space 72 forms a space for porcelain material. The casting mold 67 with the burned out wax can be pre-heated as can a puck-shaped unit of porcelain material. The pre-heating temperature for a cap of the Procera AllCeram type can be chosen within the temperature range of 750-900° C. In the case of a cap of the Procera AllZirkon type, a pre-heating temperature of 550-750° C. can be chosen. A pre-heating time of 30 minutes to 6 hours can be used. In step 71, the cap is indicated by 73.

In a step 74, said cylinder-shaped porcelain material 75 is applied via a recess 76 which was obtained in step 71. The porcelain material is pressed in the direction of arrow 77. The heated porcelain cylinder or porcelain puck is pressed into the casting mold under vacuum and at high temperature. This is followed by cooling to room temperature. The press time can be up to 40 minutes. It is conceivable to apply a vacuum of 50 hPa. The press temperature for a cap of the Procera AllCeram type can be 850-1200° C. The press temperature for a cap of the Procera AllZirkon type can be chosen within the range of 700-1000° C.

Casting according to FIG. 5 is followed by demolding and inspection. Step 78 involves demolding of the embedding compound by blasting, for example. The embedding compound is indicated by 79. The shape of the dental crown 81 emerges in step 80. In this state 81, the dental crown can be delivered to the customer, see 23, 24 in FIG. 1. The casting channel 83 can be cut off by the customer. The crown can be fitted in a jaw model which has been created by the establishments 4, 9. This is followed, if appropriate, by coloring and polishing, preferably done at the dental laboratory or the establishment 9 according to FIG. 1.

Figure 6:
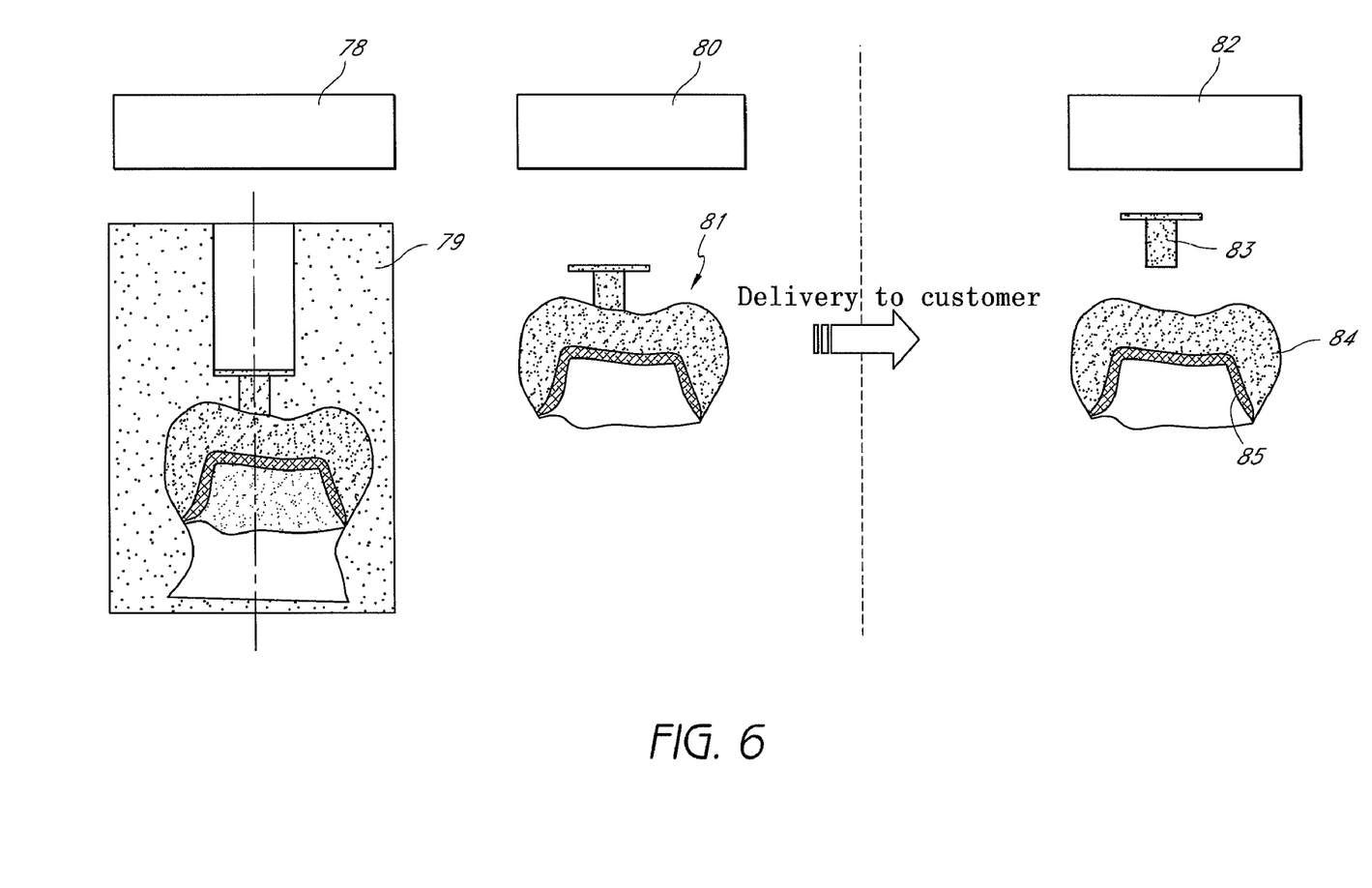
FIG. 6 is a diagrammatic representation showing, in three steps, demolding, inspection and working, by the customer, of a cast dental crown.

Thus, a dental replacement component is obtained in the form of a dental crown or dental bridge, cf. FIG. 6, which forms an integrated unit with two layers 84, 85. The first layer 84 consists of or comprises porcelain material which forms or is included in the outer shape or most of the outer shape of the dental crown (before the final shaping in the patient's mouth). The second layer consists of or comprises a material 85 different than the porcelain material and forms a cap. The accuracy can be considerable, for example 0.02-0.1 mm.

The description above also points to an arrangement for a preliminary stage of construction of a dental replacement component 81 in FIG. 6. The replacement component consists of a dental crown with integrated outer and inner layers 84, 85, where the outer layer is intended to form the outer shape of the dental crown and consists of porcelain material, and the inner layer is intended to form a cap in the dental crown/porcelain material. The layers are integrated with the aid of a heatable cylinder-shaped unit, see 75 in FIG. 5. The cylinder-shaped unit or puck can be pressed against the cap under vacuum and at high temperature.

The invention is not limited to the embodiment set out above by way of example, and instead it can be modified within the scope of the attached patent claims and the inventive concept.

What is claimed is:

1. A method for producing a dental crown or bridge, the method comprising:
   creating a first information item based upon a treatment situation in a patient's mouth, the first information item including an outer surface at the treatment situation;
   viewing the treatment situation and generating a second information item corresponding to a dental crown or bridge based at least in part upon the first information item, the second information item including at least the inner and outer surfaces of the dental crown or bridge;
   sending the second information item to a substantially fully automated production arrangement;
   receiving a dental crown or bridge comprising at least an outer layer and an inner layer, the inner layer forming a cap with an inner shape that matches to the outer shape in the treatment situation;
   wherein the substantially fully automated production arrangement is configured to produce a cap and a die in embedding compound with an inner shape of the cap, to apply an adhesive to the inner shape, mount the cap on the die, scan the cap and the die, immerse the cap and the die in molten wax, mill the outer shape of the dental crown from the hardened molten wax, and apply a casting channel to the shaped molten wax.

2. The method of claim 1, wherein the substantially fully automated production system is configured to perform a casting process in which an embedding compound is applied in a cuvette, wax is burned out, and a cylinder-shaped unit or porcelain material is pressed into the casting mold under vacuum and at high temperature and bring about subsequent cooling to room temperature.

3. The method of claim 1, wherein the substantially fully automated production system is designed to bring about a demolding of the embedding compound with the aid of blasting, inspection, and packaging for delivery to the customer.

4. The method of claim 1, wherein the dental crown is configured such that an establishment external to the substantially fully automated production arrangement cuts off the casting channel, fits the crown in a jaw model and/or colors or polishes the crown.

5. A method for producing a dental crown or bridge, the method comprising:
   receiving data corresponding to a dental crown or bridge based, at least in part, upon information gathered from a treatment situation in a patient's mouth that includes at least an outer surface at the treatment situation, the data including at least the inner and outer surfaces of the dental crown or bridge; and
   with a substantially fully automated production arrangement, producing by pressing or pressure-casting a dental crown or bridge comprising two layers, the first layer comprising a porcelain material that forms a portion of an outer surface of the dental crown or bridge, and the second layer comprising a densely sintered material different than the porcelain material, the second layer forming a cap with an inner surface that matches to the outer shape in the treatment situation;
   wherein the substantially fully automated production arrangement is configured to produce a cap and a die in embedding compound with an inner shape of the cap, to apply an adhesive to the inner shape, mount the cap on the die, scan the cap and the die, immerse the cap and the die in molten wax, mill the outer shape of the dental crown from the hardened molten wax, and apply a casting channel to the shaped molten wax.

6. The method of claim 5, wherein the substantially fully automated production system is configured to perform a casting process in which an embedding compound is applied in a cuvette, wax is burned out, and a cylinder-shaped unit or porcelain material is pressed into the casting mold under vacuum and at high temperature and bring about subsequent cooling to room temperature.

7. The method of claim 5, wherein the substantially fully automated production system is designed to bring about a demolding of the embedding compound with the aid of blasting, inspection, and packaging for delivery to the customer.

8. The method of claim 5, wherein the dental crown is configured such that an establishment external to the substantially fully automated production arrangement cuts off the casting channel, fits the crown in a jaw model and/or colors or polishes the crown.

9. A method for producing a dental crown or bridge, the method comprising:
   creating a first information item based upon a treatment situation in a patient's mouth, the first information item including an outer surface at the treatment situation;
   viewing the treatment situation and generating a second information item corresponding to a dental crown or bridge based at least in part upon the first information item, the second information item including at least the inner and outer surfaces of the dental crown or bridge;
   sending the second information item to a substantially fully automated production arrangement;
   receiving a dental crown or bridge comprising at least an outer layer and an inner layer, the inner layer forming a cap with an inner shape that matches to the outer shape in the treatment situation;
   wherein the substantially fully automated production arrangement is configured to produce a cap, mill a die corresponding to an outer shape of the cap, immerse the milled die in molten wax, mill the outer shape of the dental crown in the hardened wax, separate the wax mold and the die, mount the wax mold and the cap together, and apply a casting channel to the wax mold.

10. The method of claim 9, wherein the substantially fully automated production system is configured to perform a casting process in which an embedding compound is applied in a cuvette, wax is burned out, and a cylinder-shaped unit or porcelain material is pressed into the casting mold under vacuum and at high temperature and bring about subsequent cooling to room temperature.

11. The method of claim 9, wherein the substantially fully automated production system is designed to bring about a demolding of the embedding compound with the aid of blasting, inspection, and packaging for delivery to the customer.

12. The method of claim 9, wherein the dental crown is configured such that an establishment external to the substantially fully automated production arrangement cuts off the casting channel, fits the crown in a jaw model and/or colors or polishes the crown.

13. A method for producing a dental crown or bridge, the method comprising:
   receiving data corresponding to a dental crown or bridge based, at least in part, upon information gathered from a treatment situation in a patient's mouth that includes at least an outer surface at the treatment situation, the data including at least the inner and outer surfaces of the dental crown or bridge; and
   with a substantially fully automated production arrangement, producing by pressing or pressure-casting a dental crown or bridge comprising two layers, the first layer comprising a porcelain material that forms a portion of an outer surface of the dental crown or bridge, and the second layer comprising a densely sintered material different than the porcelain material, the second layer forming a cap with an inner surface that matches to the outer shape in the treatment situation;
   wherein the substantially fully automated production arrangement is configured to produce a cap, mill a die corresponding to an outer shape of the cap, immerse the milled die in molten wax, mill the outer shape of the dental crown in the hardened wax, separate the wax mold and the die, mount the wax mold and the cap together, and apply a casting channel to the was wax mold.

14. The method of claim 13, wherein the substantially fully automated production system is configured to perform a casting process in which an embedding compound is applied in a cuvette, wax is burned out, and a cylinder-shaped unit or porcelain material is pressed into the casting mold under vacuum and at high temperature and bring about subsequent cooling to room temperature.

15. The method of claim 13, wherein the substantially fully automated production system is designed to bring about a demolding of the embedding compound with the aid of blasting, inspection, and packaging for delivery to the customer.

16. The method of claim 13, wherein the dental crown is configured such that an establishment external to the substantially fully automated production arrangement cuts off the casting channel, fits the crown in a jaw model and/or colors or polishes the crown.

* * * * *